(12) United States Patent
Dookhith et al.

(10) Patent No.: US 6,342,466 B1
(45) Date of Patent: Jan. 29, 2002

(54) BIODEGRADABLE SOLUTIONS OF BIOLOGICALLY ACTIVE COMPOUNDS

(75) Inventors: Mohammad Dookhith, Charlotte, NC (US); Ralf Zerrer, Karlstein (DE); Frank Weinelt; Franz Scherl, both of Burgkirchen (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/389,151

(22) Filed: Sep. 2, 1999

(51) Int. Cl.⁷ .......................... A01N 25/02; A01N 25/04
(52) U.S. Cl. ..................... 504/362; 504/363; 504/367; 514/772; 514/937; 514/952
(58) Field of Search ................. 504/362, 363, 504/367; 514/772, 937, 952

(56) References Cited

U.S. PATENT DOCUMENTS

| | | | | |
|---|---|---|---|---|
| 2,796,423 A | | 6/1957 | Cottle et al. ............. | 260/410.9 |
| 2,842,499 A | | 7/1958 | Cottle et al. ................. | 252/52 |
| 3,563,893 A | | 2/1971 | Doelling et al. ............. | 252/73 |
| 3,944,674 A | * | 3/1976 | Nikles et al. ................ | 424/300 |
| 4,623,727 A | | 11/1986 | Hübele ........................ | 546/178 |
| 4,707,182 A | * | 11/1987 | Martin et al. .................. | 71/94 |
| 4,881,966 A | | 11/1989 | Nyffeler et al. ................ | 71/94 |
| 4,891,057 A | | 1/1990 | Sohn et al. ..................... | 71/72 |
| 4,902,340 A | | 2/1990 | Hubele ........................... | 71/94 |
| 5,314,863 A | | 5/1994 | Löher et al. ................. | 504/100 |
| 5,861,506 A | * | 1/1999 | Simon et al. ................. | 536/66 |

FOREIGN PATENT DOCUMENTS

| | | |
|---|---|---|
| DE | 25 46 845 | 4/1977 |
| EP | 0159 290 | 10/1985 |
| EP | 0 333 131 | 9/1989 |
| EP | 0 346 620 | 12/1989 |
| WO | WO 91/07874 | 6/1991 |
| WO | WO 91/08202 | 6/1991 |

OTHER PUBLICATIONS

H. F. Fink and G. Koerner, technischen Chemie Ullmann's Encyclopedia of Industrial Chemistry, 4$^{th}$ revised and extended edition, Verlag Chemie, Weinheim, vol. 20, pp. 411–414, 1972.

W. Schönfeldt, "Grenzflächenaktive Alkylenoxid–Addukte [Interface–active Alkylene Oxide Adducts]"Wissenschaftliche Verlagsgesellschaft MBM, Stuttgart 1973, pp. 805–853.

* cited by examiner

Primary Examiner—S. Mark Clardy
(74) Attorney, Agent, or Firm—Scott E Hanf

(57) ABSTRACT

The disclosure pertains to bio-active preparations, as solutions, emulsions, suspensions suspoemulsions, emulsifiable concentrates, and dispersible granules where the biologically active compound is dissolved in a solvent the general formula RCH(OR')$_2$, ketals of the formula R$_2$C(OR')$_2$, or orthoesters of the formula RC(OR')$_3$, wherein the substituents are defined herein. Acetal from monoaldehyde and alcohol have the

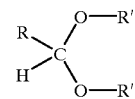

(I)

general formula (I)

Acetals used herein also include structures such as:

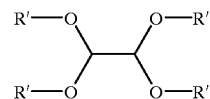

And more complex acetal compounds as disclosed herein.

The biologically active compounds in such preparations are active organic compounds, in particular, herbicides and safeners, insecticides, fungicides, acaricides, nematicides, pheromones and repellents. Embodiments included are oil-in-water (O/W) emulsions, emulsifiable concentrates(EC), water dispersible granules (WG) and suspoemulsion (SE). The bio-active/acetal formulations provide enviro-safe treatments as formulated herbicides, safeners, insecticides, fungicides, acaricides, nematicides, pheromones and repellents and exhibit low flammability and biodegradability.

19 Claims, No Drawings

BIODEGRADABLE SOLUTIONS OF BIOLOGICALLY ACTIVE COMPOUNDS

FIELD OF THE INVENTION

The invention relates to solutions, solid and liquid dispersions, and emulsions of biologically active organic compounds, in particular, herbicides and safeners, insecticides, fungicides, acaricides, nematicides, pheromones and repellents, and more particularly, insecticidal active substances.

BACKGROUND OF THE INVENTION

Formulations of herbicidal, fungicidal or insecticidal active substances typically employ adjuvants, such as solvents, inert fillers, such as chalk, kaolin or silica, in particular surface-active substances. These formulations enable the preparations to wet substrates well and/or allow easy dispersion in water when they are used. In the case of the water-dispersible granules, adjuvants allow rapid disintegration after introduction into water.

There are processing and application problems associated with the preparation of formulated bio-active compounds, especially those having a relatively low melting point of 100° C. and below. The prior art suggests a variety of solvents used in conjunction with these substances. Suitable suggested solvents are the high-boiling alkylbenzenes and xylenes, 1- or 2-methylnaphthalene, dimethylnaphthalenes, and other polynuclear aromatic compounds. Other water-immiscible solvents suggested include paraffin oils, vegetable oils, alicyclic compounds, alkanols, such as cyclohexanol and isooctyl alcohol, ethers, ketones, such as cyclohexanone, 4-methylcyclohexanone and isophorone, and esters, such as ethyl benzoate and tri-n-butyl phosphate. Many of these solvents have a low flash point temperature and are bioaccumulative, presenting hazards and toxicity problems.

Surprisingly, a class of organic solvent has been found to be highly effective for dissolving organic bio- active compounds, which has generally a high flash point, and is not bioaccumulative. The invention provides a solvent for formulated bio-active compounds that bio-degrades into non-hazardous, and is non-bioaccumulative.

SUMMARY OF THE INVENTION

The invention therefore relates to bio-active preparations, as solutions, solid or liquid dispersions, suspensions and emulsions comprising a bio-active compound and a water soluble or oil soluble acetal. Particular exemplary embodiments include emulsifiable concentrates (EC), water dispersible granules (WG), and suspoemulsions.

An further object of the present invention is to provide oil-in-water (O/W) emulsions of bio-active compounds and acetal in the oil phase, in stable colloidal dispersion in water.

Another object of the present invention is to provide formulated bio-active compounds characterized as having low volatility, high flash point and which are toxicologically safe.

DETAILED DESCRIPTION OF THE PREFERRED EMBODIMENTS

Broadly, the bio-actives in solution, dispersion, emulsion or adsorption onto solids, together with acetals according to the present invention are active organic compounds, in particular, herbicides and safeners, insecticides, fungicides, acaricides, nematicides, pheromones and repellents.

The active substances, can be supplied in the form of liquid or solid formulations, containing bioactive substance content as a rule at from 1 to 80% by weight, preferably 5 to 60% by weight. The biologically active organic compounds mixed with acetal according to the invention, preferably include herbicides and safeners, insecticides, fungicides, acaricides, nematicides, pheromones and repellents, in particular bio-active substances, include glufosinate-ammonium, glyphosate, bialaphos; active substances from the phenoxy series, such as CMPP, MCPA, 2,4-D, active substances from the phenoxyphenoxy series, such as diclofopmethyl, or the heteroaryloxyphenoxy series, such as fenoxaprop-ethyl, fenoxaprop-P-ethyl; active substances from the urea series, such as isoproturon, diuron, linuron, monolinuron and chlortoluron, active substances from the series comprising the sulfonylureas, such as amidosulfuron, tribenuron (DPX-L5300), thiameturon-methyl (DPX-M6316), metsulfuron-methyl (DPX-T6376), primisulfuron-methyl and nicosulfuron; active substances from the series comprising the triazines, such as atrazine or simazine, active substances from the series comprising the imidazolinones, such as Imazapyr, Imazaquin, Imazethapyr and Imazamethabenz, and diphenyl ether derivatives, for example Acifluorfen, Fluoroglycofen, Lactofen and Bifenox, dicotylene herbicides, for example Ioxynil, Bromoxynil, Dicamba, Diflufenican, Fluroxypyr, Phenmedipham, Desmedipham, Bentazone, Metamitron, Metribuzin, Chloridazon, Ethofumesate or the active substance Trifluralin; and safenets, such as, for example, the compounds described in EP-A-86750, EP-A-94349, EP-A-191736, EP-A-346620, EP-A-333131, EP-A-269806, EP-A-159290, DE-A-2546845, PCT/EP-90/02020 and PCT/EP-90/01966; fungicidal active substances, such as, for example, active substances from the series comprising the azoles, for example Triadimefon, Cyproconazole, Myclobutanil and Dichlobutrazol; active substances from the series comprising the dithiocarbamates, such as Maneb, Zineb and Mancozeb, the benzimidazoles, for example Carbendazime, or active substances such as, for example, Procymidone, Iprodione, Vinchlozoline, Thiophanate-methyl, Cymoxanil, Folpet, copper oxychloride, sulfur or TPTH.

Pesticides used herein include, as non-limiting examples, active substances from the following chemistries: Avermectin, chloroacetanilide, azole, benzonitrile, phenoxies, imidazolinone, nitroaniline, pyrrole, organophosphorous, sulfonylurea, and benzimidazole.

Active substances are known and are described in "Pesticide Manual" (by the British Crop Protection Council) or in "Farm Chemicals Handbook 91" (Meister Publishing Company, Willoughby, Ohio), both of which are hereby incorporated by reference.

Specific examples of pesticidal substances used in conjunction with the acetal solvent according to the invention are particulary those with melting points below about 100° C., and there may be mentioned by way of examples, Phosalone, The Aclonifenoxadiazon mixture, Aclonifen-Linuron, Aclonifen-Bifenox, Bifenox, Acephate, Aclonifen, Alachlor, Aldicarb, Amethryn, Aminocarb, Amitraz, Azamethiphos, Azinphos-Ethyl, Azinphos-Methyl, Aziprotryne, Benolaxyl, Benfluralin, Bensulide, Bensultap, Benzoximate, Benzoylprop-Ethyl, Bifenthrin, Binopacryl, Bromophos, Bromo-Propylate, Bromoxynil Esters, Bupirimate, Buthiobate, Butocarboxim, Carboxin, Chlorbufam, Chlordimeform, Chlorfenson, Chlormephos, Chlorobenzilate, Fluorochloridone, Chloropropylate, Chlorphoxim, Chlorpropham, Chlorpyrifos, Chlorpyrifos-Methyl, Cloethocarb, Cyanophos, Cycloate, Cycloxydim, Cyfluthrin, Demethon-S-Methyl, Desmetryn, Dialifos, Diazinon, Diclofop, Dicofol, Diethatyl, Dimethachlor, Dimethomethryn, Dimethoate, Dinobuton, Dinoseb, Dioxabenzofos, DNOC (2-Methyl-4,6-Dinitrophenol), EPN (O-Ethyl O-(4-Nitrophenyl)-Phenylphosphonothioate), Etaconazole, Ethalfluralin, Ethiofencarb, Ethofumesate, Famphur, Fenamiphos, Fenitropan, Fenobucarb, Fenothiocarb, Fenoxaprop, Fenoxycarb, Fenpropathrin, Fenson, Flanuprop, Fluchloralin, Fluorodifen, Fluoroglycofen, Flurecol, Fluroxyupyr, Formothion, Furolaxyl, Furmecyclox, Haloxyfop, Heptenophos, Hymexazol, Iodofenphos, Ioxynil Esters, Isoprothiolane, Linuron, Metalaxyl, Metazachlor, Methamidophos, Methidathion, Methopotryne, Metolcarb, Monalide, Monocrotophos, Monolinuron, Myclobutanil, Napropamide, Nitrapyrin, Nitrofen, Nitrothalisopropyl, Oxabentrinil, Oxadiazon, Oxyfluorfen, Parathion-Methyl, Penconazole, Pendimethalin, Pentanochlor, Phenthoate, Phosfolan, Phosmet, Piproctanil, Pirimicarb, Prochloraz, Profluralin, Promecarb, Prometon, Propachlor, Propamocarb, Propanil, Propetamphos, Propham, Propoxur, Propthoate, Pyrazophos, Pyridate, Quinalphos, Quizalofop, Resmethrin, Secbumeton, Simetryn, Tebutan, Tefluthrin, Temephos, Tetramethrin, Tetrasul, Thiofanox, Tolciofos-Methyl, Triadimefon, Trichlorfon, Tridiphane, Triflumizole, Trifluralin, And Xylylcarb.

Other pesticides with melting points below 100° C. which can advantageously be used in the compositions of this invention include the various esters of the class of phenoxy-alkanoic acids. These include for example:

2,4-D: (2,4-dichlorophenoxy) acetic acid esters;

2,4-DB: 4-(2,4-dichlorophenoxy) butyric acid esters;

2,4-DB: 2-(2,4-dichlorophenoxy) propionic acid esters and their optical isomers;

MCPA: (4-chloro-2-methylphenoxy) acetic acid esters;

MCPB: 4-(4-chloro-2-methylphenoxy) butyric acid esters; or

Mecoprop: 2-(4-chloro-2-methylphenoxy) propionic acid esters and their optical isomers.

In the formulation of lipophilic pesticidal compound as aqueous preparations or organic preparations, and in cases where high melting acetals are employed, co-solvent or diluent may be included therewith, especially if the selected acetal solvent has partial solubility in water. Within the scope of the present invention, the term "co-solvent", means a solvent other than acetal and may be a single other solvent or a mixture of several solvents other than acetal in combination with the acetal. Organic co-solvent usually is not needed, and if present, is used in a weight ratio of solvent (s):acetal of 1:10 to 10:1, or whatever amount of solvent to be used which suitably cooperates with the acetal to form a solution of lipophilic pesticidal substance, and partition in the organic and/or aqueous phase.

Acetals used in the present invention are conventionally made by the elimination of water from an aldehyde group containing- compound and hydroxy group- containing compound, esp. an aldehyde and alcohol, under acidic conditions. Acetals from monoaldehyde and a single mono-alcohol have the general structure of (I):

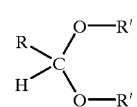

(I)

The R group can be branched or unbranched, saturated or unsaturated and aliphatic or aromatic. Preferably, R is $C_1$- to $C_{20}$-aliphatic, more preferably $C_4$–$C_{12}$ aliphatic groups. The acetals can be made from a reaction in a stoichiometric amount of one ore more alcohols with the aldehyde or in a mole ratio greater than stoichiomretric 2:1, e.g.2.5 or even 3:1 to 5:1 moles of alcohol:aldehyde. A single alcohol and aldehyde can be used, or a mixture of different alcohols with a single aldehyde, or mixture of aldehydes with a single alcohol, or a mixture of both different alcohols and different aldehydes be used. Acetals used herein may have a total of 3 to 50 carbon atoms, but more practically from 5 to 30 carbon atoms. Preferred acetals have a boiling point of from 100° C. to 300° C. Acetals and raw materials for their preparation are disclosed in U.S. Pat. Nos. 2,796,423, 2,842, 499, and 3,563,893 which are hereby incorporated by reference.

Included in the definition of the term "aldehyde" herein are divalent aldehydes (dialdehydes), especially those having 2 to 10 carbon atoms. Dialdehydes such as glyoxal, tartaric acid dialdehyde, succinic dialdehyde, maleic acid dialdehyde and fumaric acid dialdehyde are particularly suitable for preparing the acetals used according to the invention. Acetal derived from glyoxal and alcohol has the general

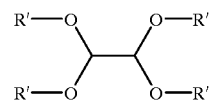

structure:

Wherein R' has the meaning ascribed above.

Alcohol means mono- or poly-hydroxy compounds. Thus, alcohol can be monohydric or polyhydric (2 to 20—OH groups), an alkanolamine, an alkoxylated (EO and or PO) alcohol, or carboxylated, acylated, or etherified- mono or -polyols, and each R' independently of one another can contain from 1 to 24 carbon atoms, preferably 4 to 12 carbon atoms, unsubstituted or substituted with O, N or S-containing groups. Alcohols can have R' groups that are branched or unbranched, substituted or unsubstituted, saturated or unsaturated, cyclic or acyclic, and aliphatic or aromatic. Examples of mono-, di- and trihydric alcohols are methyl-, ethyl-, n-propyl-, n-butyl-, i-butyl-, sec-butyl-, tri-hydroxy propane, glycerol, trimethylol propane, amyl-, octyl-, ethylhexyl, decyl-, octadecyl- alcohol, to name but a few of the myriad mono- or polyols. Exemplary cyclic alcohols include tetrahydrofurfuryl alcohol, cyclohexanol, cycloheptanol, cyclooctanol, 2-methylcyclohexanol, 3-butylcyclohexanol, and 3-methylcyclohexanol. Examples of ether alcohols are lower ($C_1$–$C_{10}$, i.e. methyl, ethyl, propyl, butyl, pentyl, hexyl, stc.) alkyl ethers of mono, di or tri ethylene or propylene glycol.

Oxygenated aldehyde, e.g. alkoxy substituted, or non-oxygenated aldehyde can be used.

Specific acetal embodiments for use in the presentation are:

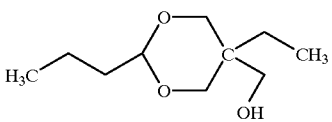

from butyraldehyde and 1,2,3-trihydroxy propane; and

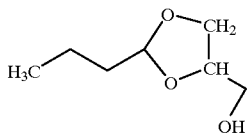

from butyraldehyde and 1,1,1-trimethylol propane; and

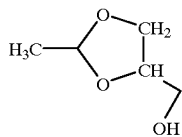

from paraldehyde and 1,2,3-trihydroxy propane; and

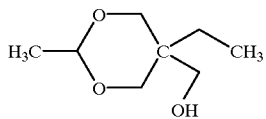

from paraldehyde and 1,1,1-trimethylol propane with a mole ratio of 0.33:1; and

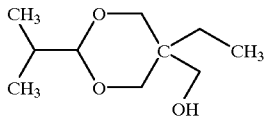

from isobutyraldehyde and 1,1,1-trimethylol propane reacted in a mole ratio of 1:1; for example.

Included within the meaning of acetals of the formula RCH(OR')$_2$, are ketals which have the formula R$_2$C(OR')$_2$, wherein R$_2$ is defined as for R above; and orthoesters which have the formula RC(OR')$_3$, wherein these R, and R' groups have the same meaning as above as for ketals and orthoesters such as linear, or branched alkyl and substituted and unsubstituted cycloalkyl. Exemplary R and R' groups are methyl, ethyl, n-propyl, n-butyl, i-butyl, sec-butyl, amyl, octyl, decyl, octadecyl, etc. When R is cycloalkyl, it may typically be cyclohexyl, cycloheptyl, cyclooctyl, 2-methylcycloheptyl, 3-butylcyclohexyl, 3-methylcyclohexyl, etc. R may be inertly substituted i.e. it may bear a non-reactive substituent such as alkyl, cycloalkyl, ether, halogen, etc. Typically inertly substituted R groups may include 3-chloropropyl, 2-ethoxyethyl, carboethoxymethyl, 4-methyl cyclohexyl, etc. The preferred R groups may be lower alkyl, i.e. $C_1$–$C_{10}$ alkyl, groups including e.g. methyl, ethyl, n-propyl, i-propyl, butyls, amyls, hexyls, octyls, decyls, etc. R and R' may preferably be butyl, isobutyl, 2-ethylhexyl in the case of ketal.

Exemplary oxygenated acetals used in the invention may be formed by reacting methoxyacetaldehyde with tetrahydrofurfuryl alcohol or with mono lower alkyl ethers of mono, di or tri ethylene or propylene glycols to form complex acetals.

Other exemplary complex acetals are:
methoxyacetaldehyde di(alkoxydiethoxyethyl) acetal,
methoxyacetaldehyde di(alkoxyethyl) acetal,
methoxyacetaldehyde di(alkoxyethoxyethyl),
methoxyacetaldehyde di(alkoxydiethoxyethyl) acetal.

Other complex acetals are formed by reacting methoxyacetaldehyde with mono alkyl ethers of mono, di or tri propylene glycols.

In forming the above described acetals from an aldehyde, conventional preparation methods can be used. Thus, each 1 mole of aldehyde is reacted with at least 2 mols, and preferably with a small stoichiometric excess of the particular alcohol or alcohol mixture. The reaction is carried out at elevated temperatures in the presence of a catalyst which may be an acid such as hydrochloric or p-toluene sulfonic acid or the catalyst may be boron trifluoride-ethyl ether complex as is known in the art. In general, the reaction temperatures may vary from about 190° F. to about 250° F. in order to form the acetal product at a reasonably rapid rate. The reactants may be dissolved in a suitable solvent, for example, benzene or other organic solvents, and both the solvent and the water formed during the course of the reaction, as the same evaporate from the reaction mixture, may be trapped and collected by a reflux condenser.

The proportion of acetal in the bioactive formulation can be up to 90% by weight, but in general from 10% to 75% by weight, and preferably 20% to 50% by weight and in particular 40% to 60% by weight acetal is contained in formulated embodiments.

In addition to the said active substances, and acetal, formulations usually employ surfactants, wetting agents, defoamers and also, optionally, further conventional formulating auxiliaries such as agglomeration auxiliaries, stabilizers and fillers. Specifically, the present formulations can optionally contain 2 to 60% by weight, preferably 5 to 50% by weight, of one or more wetting agents. Wetting agents, preferably are among the group of alkanesulfonates, alkylnaphthalenesulfonates, alkylbenzenesulfonates, alkylpolyglycol ether-sulfonates, alkylsulfosuccinic acid half-esters, fatty acid N-methyltaurides, fatty alcohol ethoxylates, ethylene oxide-propylene oxide block copolymers, or mixtures of the above wetting agents.

In addition to the said active substance, acetal and wetting agents, formulations can also contain antifoam compounds. Exemplary antifoams are described, for example, by H. -F. Fink and G. Koerner in technischen Chemie Ullmann's Encyclopedia of Industrial Chemistry]", 4th revised and extended edition, Verlag Chemie, Weinheim, Volume 20, page 411–414, and by W. Schönfeldt in "Grenzflächenaktive Alkylenoxid-Addukte [Interface-active Alkylene Oxide Adducts]", Wissenschaftliche Verlagsgesellschaft MBM, Stuttgart 1973, pages 805–853, each of which are incorporated herein by reference. Solid antifoams, include for example, aluminum stearate. Liquid antifoams include perfluoroalkyl phosphinic-phosphononic acid.

Exemplary formulations of dissolved bio-active compound in acetal are, liquid oil-in-water (O/V) emulsions, liquid water-in-oil emulsions, emulsifiable concentrates (EC), suspoemulsions (SE), and water dispersible granules (WG), such forms as are recognized in the art.

In a solution formulation, the bio-active and acetal are directly mixed with or without co-solvent. Exemplary co-solvents are aromatic or aliphatic compounds, such as SOLVESSO 150, N-methyl pyrrolidone; methylated oils, such as methyl esters of soybean oil, cottonseed oil or rapeseed oil, or paraffin oils.

Emulsifiable concentrates (EC) are defined as a solution of bio-active in the acetal solvent in combination with one or more surfactants. Generally from 20 to 80% (by weight) of acetal, from 0.5 to 20% of bio-active compound and from 5 to 15% of surfactant are included in EC form.

Suspoemulsions (SE) are defined as a dispersion of solids and oil droplets dispersed in an aqueous continuous phase. The bio-active may be suspended as undissolved solid or dissolved in the oil phase, or dispersed phase oil phase and/or dissolved in or suspended in the aqueous phase.

Water dispersible granules (WG) are defined as a bio-active which is dissolved in acetal and adsorbed or absorbed with a solid carrier. Solid carriers known in the art include starches, clays, and silicas, including mixtures, and the like. WG's can optionally contain wetting or dispersing agents, all of which are well known in the art. The WG is formed by making a solution of the bio-active in acetal, the solution is sprayed or mechanically mixed and pelletized or granulated in the conventional manner. Generally water dispersible granules comprise 0.5 to 50% of bio-active, 10% to 50% of acetal, 5% to 30% surfactant. The surfactants usable therewith are anionic, nonionic, zwitterionic, and cationic surfactants.

For formulated bio-active—acetal mixtures in the form of emulsions, it is preferred to choose an emulsifying system made up of anionic, nonionic, or cationic surfactants or mixtures of anionic and nonionic, or nonionic and cationic surfactants. Also, two nonionic surface-active agents can be employed, one having a more hydrophilic balance and the other a more lipophilic or hydrophobic balance. Particularly preferred amongst the hydrophobic surfactants are those which have a low HLB (hydrophilic-lipophilic-balance) and can act to prevent or inhibit crystal growth of a lipophilic bio-active ingredient. This is best achieved when the hydrophobic surfactant mixes with and/or solubilizes in the active ingredient-acetal mixture to render a liquid or a surfactant which significantly lowers the melting point thereof. Especially advantageous for this use are the hydrophobic ethoxylated nonylphenol surfactants described above, or polyoxyalkylated amines, or carboxylic acids or esters.

Thus, among the surface-active agents referred to above that are chosen in a nonionic emulsion system, in the case of the hydrophilic agents, those which contain at least 7 alkylene oxide units; whereas surface-active agents containing fewer than 7 alkylene oxide units are chosen in the case of lipophilic surface-active agents.

In addition to the O/W, it is advantageous to incorporate an anionic surfactant like sulphonic acids, such as long-chain alkylbenzene sulphonates, optionally in the form of amine or ammonium salts. For example, ammonium dodecylbenzenesulphonate is advantageously employed. With reference to the emulsion compositions described above, between about 0 and 10 g/liter, preferably about 2 to 10 g/liter of the anionic surfactant is employed.

The following examples illustrate working embodiments of the invention without restricting the invention thereto. The percentages or parts are by weight.

EXAMPLE 1

EXAMPLE 1

Water Dispersible Granule a) Solution for preparing the granules a liquid solution of the following composition is prepared:

D,L-fenoxaprop-ethyl, technical grade, 96.8% is dissolved in di-2-ethylhexanol dimethyl acetal (Hostafluid V-4120) in a weight ratio of 1:2 (active:solvent) to make 95 parts;

5 parts total of a 50:50 mixture of an anionic and nonionic emulsifier mixture are added (calcium dodecylbenzene sulfononate and ethylene oxide-propylene oxide block copolymer) ) making up 100 parts by weight of the oil phase.

The oil phase is adsorbed onto a mixture of the remaining components:

10–30 parts Na $C_{14}$–$C_{19}$—α-olefin sulfonate (Hostapur® OS, Clariant);

0.1–0.5 parts defoamer (perfluorinated alkyl phosphinic/phosphonic acid—FLUOWET PL-80—Clariant);

3–5 parts of a cresol/formaldehyde condensation product as dispersant (Dispersing Agent S-1494, Clariant);

3–5 parts oleyl methyl tauride wetting agent (Hostapon® T-Clariant); and

10–20 parts of powdered fumed silica b) Preparation of the granules

The components are mixed in a ribbon blender (optionally with up to 5–10 parts of water) and granulated using any of the following methods:

Extrusion, pan granulation, or high shear mixing.

The resulting granules are dried 50–80° C. to a moisture content of less than about 1.5%. In this manner, suitable water-dispersible granules are obtained with a minimum of volatilization during processing, a product having high relative flash point, and ease of applying heat.

EXAMPLE 2

Emulsifiable Concentrate

The components:

Fipronil (15% wt./wt.)

Emulsogen 35 10 (butanol EP-PO block copolymer)

Phenyl sulfonate (alkylbenzene sulfonate-calcium salt (3% by wt.

Acetal (Hostafluid 4120) up to 100%

Are mixed in a vessel with sufficient heat and agitation to effect dissolution.

The solution is filtered and ready for use.

EXAMPLE 3

EW—OIL-IN-WATER EMULSION

A homogeneous oily mixture was obtained by mixing in a container with stirring, phosalone (350 g), isobutryaldehyde-bis-2-ethylhexyl acetal Hostafluid 4120 (250 g), and a nonylphenol ethylene oxide polycondensate (1 EO; 50 g).

Mixing in another container, with stirring and while heating to about 40° C., water (390 cc), an ethylene oxide/propylene oxide condensate (EO:PO 70:30; 40 g), melted beforehand, a dodecylbenzene sulphonate amine salt (4 g), propylene glycol (20 g), and antifoam (2 g). The aqueous mixture is homogenized. The oily mixture is then run into the aqueous mixture in a well-stirred vessel and made up to 1 liter by adding water as necessary. This mixture is then homogenized by being passed through a bead mill (1-mm glass beads) or conventional homogenizer.

Exemplary EW formulations (in g/l) are:

EXAMPLE 4

| COMPONENT | Amount (g) | |
|---|---|---|
| Phosalone, 6-chloro-3-diethoxyphosphino-Thioylthiomethyl-1,3-benzoxazol-2(3H)-one | 350 | ⎫ |
| Isobutryaldehyde-bis-2-ethylhexyl acetal | 250 | ⎬ Oily phase |
| 1:1 ethylene oxide/nonylphenol condensate | 50 | ⎪ |
| Propylene oxide/ethylene oxide condensate (EO:PO 70:30) | 40 | ⎭ |
| Dodecylbenzenesulphonic acid amine salt | 4 | |
| Propylene glycol | 20 | |
| Antifoam | 2 | |
| Balance of water up to 1.0 liter | | |

The following examples are produced using the same method.

EXAMPLE 5

| COMPONENT | Amount (g) | |
|---|---|---|
| Oxadiazon, 5-t-butyl-3-(2,4-dichloro-5-iso-propoxy-Phenyl)-1,3,4-oxadiazol-2(3H)-one | 100 | ⎫ |
| Aclonifen, 2-chloro-6-nitro-3-phenoxy-benzenamine | 300 | ⎬ Oily phase |
| Isobutryaldehyde-bis-2-ethylhexyl acetal | 300 | ⎪ |
| Alcohol ethoxylate (Genapol ® UD079) | 50 | ⎪ |
| Propylene oxide/ethylene oxide condensate (EO:PO 70:30) | 34 | ⎭ |
| Dodecylbenzenesulphonic acid amine salt | 3.4 | |
| Propylene glycol | 17 | |
| Antifoam | 1.7 | |
| Balance of water up to 1.0 liter | | |

EXAMPLE 6

| COMPONENT | Amount (g) | |
|---|---|---|
| Metalochlor, | 143 | ⎫ |
| Aclonifen, 2-chloro-6-nitro-3-phenoxy-benzenamine | 257 | ⎬ oily phase |
| Acetophenone | 150 | ⎪ |
| Isobutryaldehyde-bis-2-ethylhexyl acetal | 50 | ⎪ |
| Propylene oxide/ethylene oxide condensate (EO:PO 70:30) | 47 | ⎭ |
| Dodecylbenzenesulphonic acid amine salt | 4.7 | |
| Propylene glycol | 24 | |
| Antifoam | 2.4 | |
| Balance of water up to 1.0 liter | | |

EXAMPLE 7

Suspoemulsion

The following suspoemulsion (suspended carbaryl) using an organophosphate active ingredient was produced in g/l under the same conditions as above

| COMPONENT | Amount (g) | |
|---|---|---|
| Technical ethion, 96%, S,S'-methylenebis-(O,O-Diethylphosphorodithioate) | 261 | ⎫ |
| Isobutyraldehyde-bis-2-ethylhexyl acetal | 380 | ⎬ oily phase |
| Carbaryl | 150 | ⎪ |
| 7:1 ethylene oxide/polyaryl-phenol sulphate polycondensate (7 EO) | 50 | ⎭ |
| Mix of 3 ethylene oxide/nonylphenol polycondensates-2,7, and 10 EO (1:1:1) | 85 | |
| Balance of water up to 1.0 liter | | |

EXAMPLE 8

Emulsion with Bio-Active in Both Oil and Aqueous Phases

| COMPONENT | Amount (g) | |
|---|---|---|
| Bromoxynil octanoate | 100 | ⎫ |
| Bromooxynil heptanoate | 100 | ⎬ oily phase |
| Isobutryaldehyde-bis-2-ethylhexyl acetal | 200 | ⎪ |
| Glyphosate IPA | 225 | ⎭ |
| Propylene glycol | 30 | |
| Butanol- EO/PO copolymer (Emulsogen 3510) | 40 | |
| Antifoam (Fluowet PL-80) | 2 | |
| Suspending agent (Clay) | 15 | |

The general procedure to be used for the preparation of an emulsion wherein active ingredients are included in both the oil phase and aqueous phase (e.g. example 7) is as follows:

a. A homogeneous oil-phase is prepared by thoroughly mixing the oil-phase active ingredient(s) Bromoxynil octanoate, Bromooxynil heptanoate and solvent isobutryaldehyde-bis-2-ethylhexyl acetal. If necessary, a co-solvent, e.g. "TENNECO"(trademark) 100, 150 or 200 and, if necessary, a hydrophobic surface active agent can be used.

b. A homogenous water-phase is prepared by thoroughly mixing the water-phase active ingredient(s) and adjuvants consisting of all other ingredients, including water together with clay. While these ingredients are preferably added in the above sequence, the order can generally be that which is convenient and maintains the water-phase homogeneity.

c. The oil-phase is gradually added to the well stirred water-phase and made up to one liter by adding water if necessary. The addition may also be performed in a reverse method.

This mixture is then homogenized by passing it through a homogenizing mixer. The final oil-in-water emulsions typically have an average particle size of the dispersed oil droplets of about 2–8 microns; more preferably 3–5 microns and an overall size distribution in the range of 1–15 microns.

In a similar manner to that described above, other oil-in-water emulsions can be prepared using other water soluble active ingredients. Water soluble compounds such as:

Acifluorfen sodium: 5-[2-chloro-4-(trifluoromethyl)phenoxy]-2-nitrobenzoic acid sodium salt;

Dichlorophen sodium: 5,5'-dichloro-2,2'-dihydroxydiphenylmethane;

Glyphosinate ammonium: 4-[hydroxy(methyl)phosphinoyl]-DL-homoalanine ammonium salt;

Imazaquin ammonium: 2-(4-isopropyl-4-methyl-5-oxo-2-imidazolin-2-yl)quinoline-3-carboxylic acid ammonium salt;

Imazaquin: as the acid form in the oil phase;

Imazapyr IPA: 2-(4-isopropyl-4-methyl-5-oxo-2-imidazolin-2-yl)nicotinic acid isopropylammonium salt;

Imazapyr: as the acid form in the oil phase;

Metsulfuron: 2-[3-(4-methoxy-6-methyl-1,3,5-triazin-2-yl)ureidosulfonyl benzoic acid methyl ester, which optionally may be as a water soluble salt depending upon the pH adjustment by a neutralizing agent;

Pendimethalin: N-(1-ethylpropyl)-2,6-dinitro-3,4-xylidine; or

Chlorsulfuron: 1-(2-chlorophenylsulfonyl)-3-(4-methoxy-6-methyl-1,3,5-triazin-2-yl)urea, which optionally may be as a water soluble salt depending upon the pH adjustment by a neutralizing agent.

Bio-active formulations according to the invention that contain acetal have excellent shelf stability in the alkaline range, and formulations with bases are preferred, for example, with ammonium compounds. In the application in field use, the acetal biodegrades into toxicologically safe components.

What is claimed is:

1. A composition comprising bio-active compound and an acetal solvent, said composition is selected from the group consisting of a solution, an emulsion, a suspoemulsion and a dispersible granule.

2. The composition of claim 1 wherein said acetal has the formula

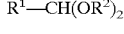

wherein $R^1$ is a branched or unbranched, saturated or unsaturated, aliphatic or aromatic $C_1$- to $C_{20}$-group, and each $R^2$ is the same or different-branched or linear alkyl group, saturated or unsaturated, aliphatic or aromatic and containing 1–25 carbon atoms.

3. The composition of claim 1, where in said acetal has the formula:

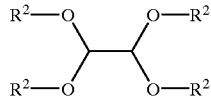

wherein each $R^2$ is the same or different, branched or linear alkyl group, saturated or unsaturated, aliphatic or aromatic and containing 1–25 carbon atoms.

4. The composition of claim 2, wherein R' contains 2 to 10 carbon atoms and each $R^2$ independently has 4 to 25 carbon atoms.

5. The composition of claim 1 further comprising a co-solvent.

6. The composition of claim 1 wherein said acetal is formed from an aliphatic or aromatic monovalent aldehyde and an aliphatic or aromatic monohydric alcohol.

7. The composition of claim 1 wherein said acetal is the reaction product of the components comprising a dialdehyde having 2 to 10 carbon atoms and a monohydric alcohol having 4 to 20 carbon atoms.

8. The composition as claimed in claim 7 wherein said dialdehyde is selected from the group consisting of glyoxal, tartaric acid dialdehyde, succindialdehyde, maleic acid dialdehyde and fumaric acid dialdehyde.

9. The composition of claim 1 wherein said bio-active is selected from the group consisting of herbicides, safeners, fungicides and insecticides.

10. The composition of claim 1 in the form of an oil in water emulsion, said emulsion contains from about 0.5 to about 50% by weight of said acetal.

11. The composition of claim 1 wherein said acetal is a reaction product of a monoaldehyde and a diol, triol or polyol.

12. The composition of claim 1 wherein said acetal has a boiling point from 100° C. to 30° C.

13. The composition of claim 1 as dispersible granules further comprising a wetting agent and optionally agglomeration auxiliaries, stabilizers and fillers.

14. The composition of claim 13 wherein said wetting agent is selected from the group consisting of alkanesulfonates, alkylnaphthalenesulfonates, alkylbenzenesulfonates, alkylpolyglycol ether-sulfonates, alkylsulfosuccinic acid half-esters, fatty acid N-methyltaurides and mixtures thereof.

15. The composition of claim 13 which contains 0.5 to 50% of bio-active, 10% to 50% of acetal, and 5% to 30% surfactant.

16. The composition of claim 15 wherein said surfactant is selected from the group consisting of anionic, nonionic, zwitterionic, and cationic surfactants.

17. The composition of claim 1 further comprising an antifoam selected form the group consisting of perfluoro-($C_6$–$C_{18}$)-alkylphosphinic acids or perfluoro-($C_6$–$C_{18}$)-alkylphosphonic acids or their alkali metal, ammonium or $C_2$–$C_{18}$-alkylammonium salts or their salts with $C_{10}$–$C_{18}$-alkylaminethoxylates or ethylenediamine-ethoxylates or mixtures.

18. The composition of claim 1, wherein said bio-active compound has a melting point below about 100° C.

19. The composition of claim 1 as a O/W emulsion, wherein the oil droplet particle size distribution is between about 1 and about 15 microns.

* * * * *